US00PP21315P3

(12) United States Plant Patent
Julien

(10) Patent No.: US PP21,315 P3
(45) Date of Patent: Sep. 28, 2010

(54) APPLE TREE NAMED 'JUGALA'
(50) Latin Name: *Malus domestica Borkh.*
Varietal Denomination: Jugala

(75) Inventor: Max Julien, Saint Paul d'Espis (FR)

(73) Assignee: International Plant Selection, Montelimar Cedex (FR)

( * ) Notice: Subject to any disclaimer, the term of this patent is extended or adjusted under 35 U.S.C. 154(b) by 12 days.

(21) Appl. No.: 12/284,917
(22) Filed: Sep. 25, 2008

(65) Prior Publication Data

US 2010/0077518 P1 Mar. 25, 2010

(51) Int. Cl.
*A01H 5/00* (2006.01)

(52) U.S. Cl. ..... Plt./162
(58) Field of Classification Search ..... Plt./162

See application file for complete search history.

(56) References Cited

OTHER PUBLICATIONS

GTITM UPOVROM Citation for 'Jugala' as per QZ PBR 20070554; Mar. 6, 2007.*

* cited by examiner

*Primary Examiner*—Kent L Bell
(74) *Attorney, Agent, or Firm*—Michelle Bos

(57) ABSTRACT

'Jugala' is a Gala-type apple characterized by its early harvest date as compared to other known Gala varieties.

5 Drawing Sheets

Latin name: *Malus domestica* Borkh.
Variety denomination: 'Jugala'.

BACKGROUND OF THE VARIETY

'Jugala' is a new and distinct variety of apple tree *Malus domestica* Borkh. This new variety is a naturally occurring whole tree mutation of 'Mitchgla' Gala (not patented). 'Jugala' was first observed in an orchard located at Saint Paul D'Espis, near Montauban in the Tarn et Garonne region of southwest France, and was selected because of its advanced coloring as compared to the surrounding 'Mitchgla' trees. 'Jugala' was asexually reproduced by budding and fruited through two successive generations in two different locations in France (Seiches sur Le Loir and VillersCotterets) and has been observed to remain true to type over successive asexually propagated generations.

BRIEF DESCRIPTION OF THE VARIETY

'Jugala' was first noted and selected for its early fruit maturity. 'Jugala' matures about five days earlier than most other known Gala varieties, 'Mitchgla' in particular. The early maturity is well characterized by a higher starch regression at harvest time, as well as a higher level of sugar and a reduction of firmness. These distinctive characteristics are shown in following tables. The comparisons were made on trees of the same age, planted in the same orchard, located in the same row side by side. All trees were planted on 'Lancep' M9 rootstock (U.S. Plant Pat. No. 7,714). Starch regression was determined using the "CTIFL Starch Conversion Chart for Apples" (G. Planton, France).

TABLE 1

'Jugala' (Row 6, trees 29 to 38) at harvest time (Aug. 20, 2007)

| Fruit number | Starch regression | Sugar (in % brix) | Firmness (in kg/cm$^2$) |
|---|---|---|---|
| 1 | 8 | 12.4 | 7.5 |
| 2 | 7 | 12.0 | 7.3 |
| 3 | 9 | 11.4 | 7.9 |
| 4 | 7 | 10.2 | 7.8 |
| 5 | 7 | 10.5 | 9.5 |
| 6 | 3 | 10.0 | 8.7 |
| 7 | 6 | 9.6 | 9.1 |
| 8 | 3 | 9.8 | 8.2 |
| 9 | 9 | 10.8 | 8.1 |
| 10 | 5 | 10.4 | 8.1 |
| 11 | 6 | 11.0 | 8.4 |
| 12 | 4 | 10.2 | 8.4 |
| 13 | 2 | 10.0 | 8.3 |
| 14 | 5 | 11.2 | 8.6 |
| 15 | 4 | 10.0 | 7.9 |
| 16 | 4 | 10.8 | 11.0 |
| 17 | 5 | 10.4 | 8.2 |
| 18 | 3 | 9.8 | 8.7 |
| 19 | 9 | 10.0 | 7.8 |
| 20 | 8 | 11.4 | 8.2 |
| Average | 5.70 | 10.60 | 8.39 |

TABLE 2

'Jugala' (Row 8, trees 59 to 69) at harvest time (Aug. 20, 2007)

| Fruit number | Starch regression | Sugar (in % brix) | Firmness (in kg/cm$^2$) |
|---|---|---|---|
| 1 | 6 | 10.4 | 8.5 |
| 2 | 8 | 11.4 | 9.2 |
| 3 | 7 | 11.0 | 7.8 |
| 4 | 8 | 10.6 | 7.7 |
| 5 | 3 | 9.8 | 8.3 |
| 6 | 5 | 10.4 | 7.9 |
| 7 | 4 | 11.0 | 9.4 |

TABLE 2-continued

'Jugala' (Row 8, trees 59 to 69) at harvest time (Aug. 20, 2007)

| Fruit number | Starch regression | Sugar (in % brix) | Firmness (in kg/cm$^2$) |
|---|---|---|---|
| 8 | 6 | 10.2 | 8.0 |
| 9 | 2 | 9.8 | 9.4 |
| 10 | 7 | 11.4 | 6.9 |
| 11 | 7 | 12.2 | 8.6 |
| 12 | 7 | 10.0 | 7.7 |
| 13 | 5 | 10.4 | 8.1 |
| 14 | 5 | 11.4 | 10.1 |
| 15 | 5 | 11.2 | 8.3 |
| 16 | 4 | 10.4 | 9.1 |
| 17 | 3 | 10.6 | 11.3 |
| 18 | 4 | 10.8 | 9.1 |
| 19 | 5 | 10.6 | 8.8 |
| 20 | 5 | 11.8 | 7.2 |
| Average | 5.30 | 10.77 | 8.57 |

TABLE 3

'Mitchgla' (Row 6, trees 69 to 78) at 'Jugala' harvest time (Aug. 20, 2007)

| Fruit number | Starch regression | Sugar (in % brix) | Firmness (in kg/crn$^2$) |
|---|---|---|---|
| 1 | 3 | 9.4 | 8.4 |
| 2 | 2 | 9.6 | 9.5 |
| 3 | 5 | 9.2 | 9.1 |
| 4 | 2 | 9.0 | 10.4 |
| 5 | 2 | 9.4 | 8.9 |
| 6 | 2 | 10.2 | 8.9 |
| 7 | 2 | 9.6 | 8.3 |
| 8 | 2 | 9.8 | 9.1 |
| 9 | 2 | 10.8 | 8.0 |
| 10 | 2 | 9.4 | 9.7 |
| 11 | 4 | 9.6 | 9.9 |
| 12 | 3 | 9.0 | 10.1 |
| 13 | 3 | 10.6 | 11.4 |
| 14 | 3 | 9.6 | 9.4 |
| 15 | 3 | 9.8 | 8.6 |
| 16 | 2 | 10.0 | 9.1 |
| 17 | 2 | 9.4 | 8.4 |
| 18 | 2 | 9.6 | 9.0 |
| 19 | 2 | 9.4 | 9.4 |
| 20 | 1 | 10.8 | 9.9 |
| Average | 2.50 | 9.71 | 9.28 |

TABLE 4

'Mitchgla' (Row 7, trees 50 to 59) at 'Jugala' harvest time (Aug. 20, 2007)

| Fruit number | Starch regression | Sugar (in % brix) | Firmness (in kg/cm$^2$) |
|---|---|---|---|
| 1 | 1 | 10.0 | 11.7 |
| 2 | 1 | 10.0 | 10.6 |
| 3 | 2 | 9.2 | 9.1 |
| 4 | 2 | 9.6 | 9.3 |
| 5 | 4 | 10.2 | 8.4 |
| 6 | 2 | 10.0 | 10.7 |
| 7 | 6 | 11.0 | 8.1 |
| 8 | 4 | 11.4 | 8.1 |
| 9 | 2 | 9.4 | 9.4 |
| 10 | 3 | 9.0 | 8.2 |
| 11 | 3 | 10.6 | 11.0 |
| 12 | 2 | 10.2 | 10.6 |
| 13 | 2 | 9.8 | 11.4 |
| 14 | 1 | 11.0 | 10.8 |
| 15 | 2 | 10.0 | 10.0 |
| 16 | 1 | 10.2 | 9.8 |

TABLE 4-continued

'Mitchgla' (Row 7, trees 50 to 59) at 'Jugala' harvest time (Aug. 20, 2007)

| Fruit number | Starch regression | Sugar (in % brix) | Firmness (in kg/cm$^2$) |
|---|---|---|---|
| 17 | 3 | 10.6 | 9.2 |
| 18 | 2 | 9.8 | 9.4 |
| 19 | 3 | 10.2 | 10.5 |
| 20 | 3 | 10.2 | 9.3 |
| Average | 2.45 | 10.12 | 9.78 |

TABLE 5

Summary of the comparison of maturity at 'Jugala' harvest time (Aug. 20, 2007)

| | Starch regression | Sugar (in % Brix) | Firmness (in Kg) |
|---|---|---|---|
| 'Mitchgla' | 2.48 | 9.92 | 9.53 |
| 'Jugala' | 5.5 | 10.69 | 8.48 |

TABLE 6

Comparison of maturity at 'Jugala' harvest time (Aug. 24, 2008) based on measurements taken from 10 fruits of each variety

| | Starch regression | Sugar (in % Brix) | Firmness (in Kg) |
|---|---|---|---|
| 'Mitchgla' | 3.2 | 10 | 8.2 |
| 'Jugala' | 6.75 | 11 | 7.65 |

Apart from its early maturity, the other characteristics of 'Jugala' relating to the tree (agronomy, shape, crop load) and the fruit (shape, color, fruit size, eating quality, storage) are similar to 'Mitchgla'.

BRIEF DESCRIPTION OF THE PHOTOGRAPHS

DETAILED BOTANICAL DESCRIPTION OF THE VARIETY

Figure 1:
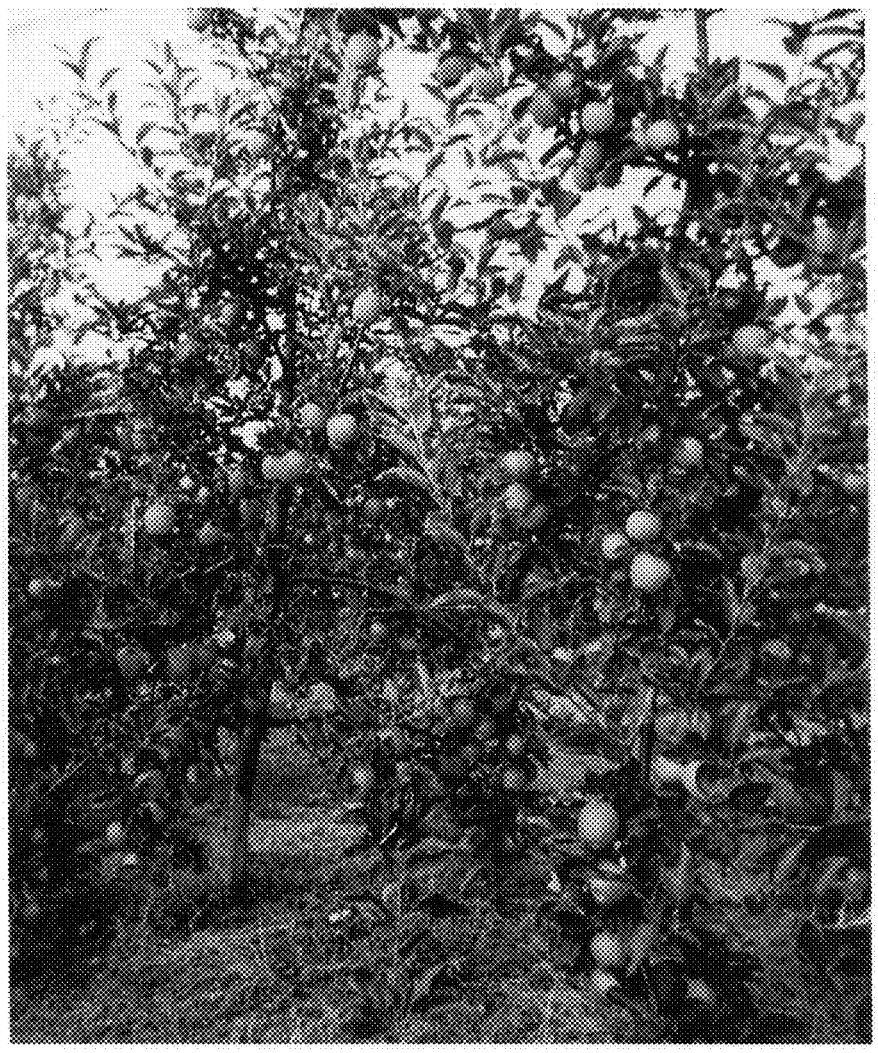
FIG. 1 shows the difference in maturity between 'Jugala' (left) and 'Mitchgla' (right), one week before harvest of 'Jugala'.
Figure 2:
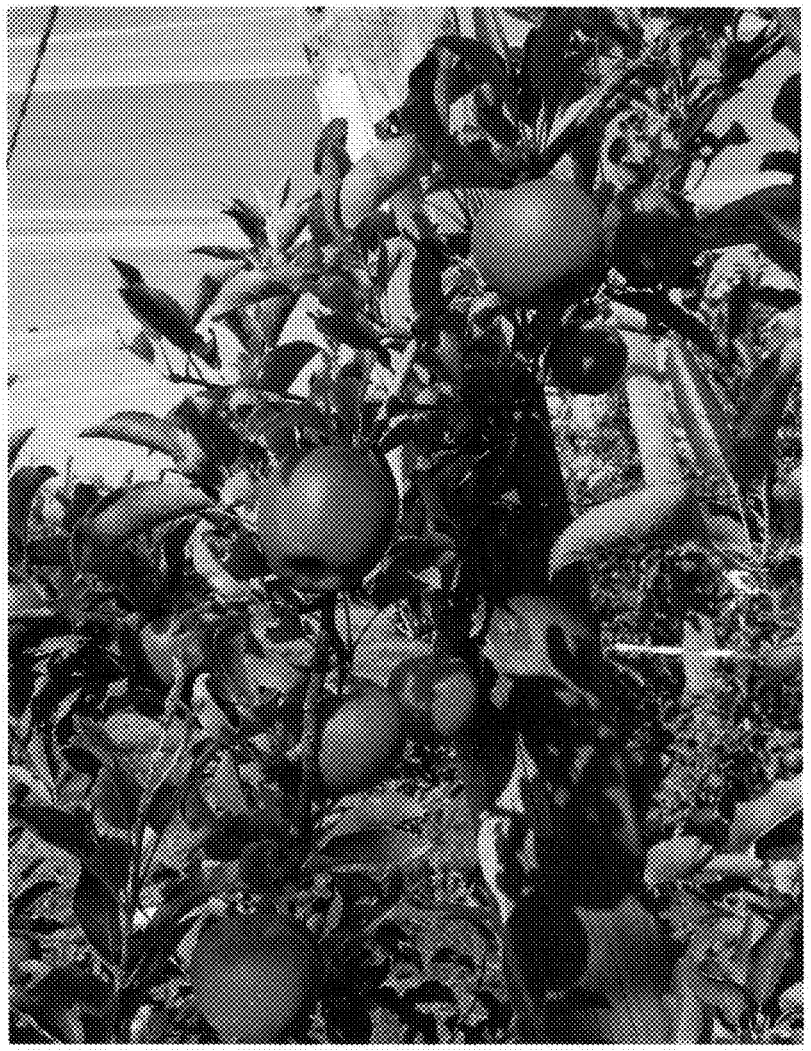
FIG. 2 shows the fruit of 'Jugala' one week before harvest.
Figure 3:
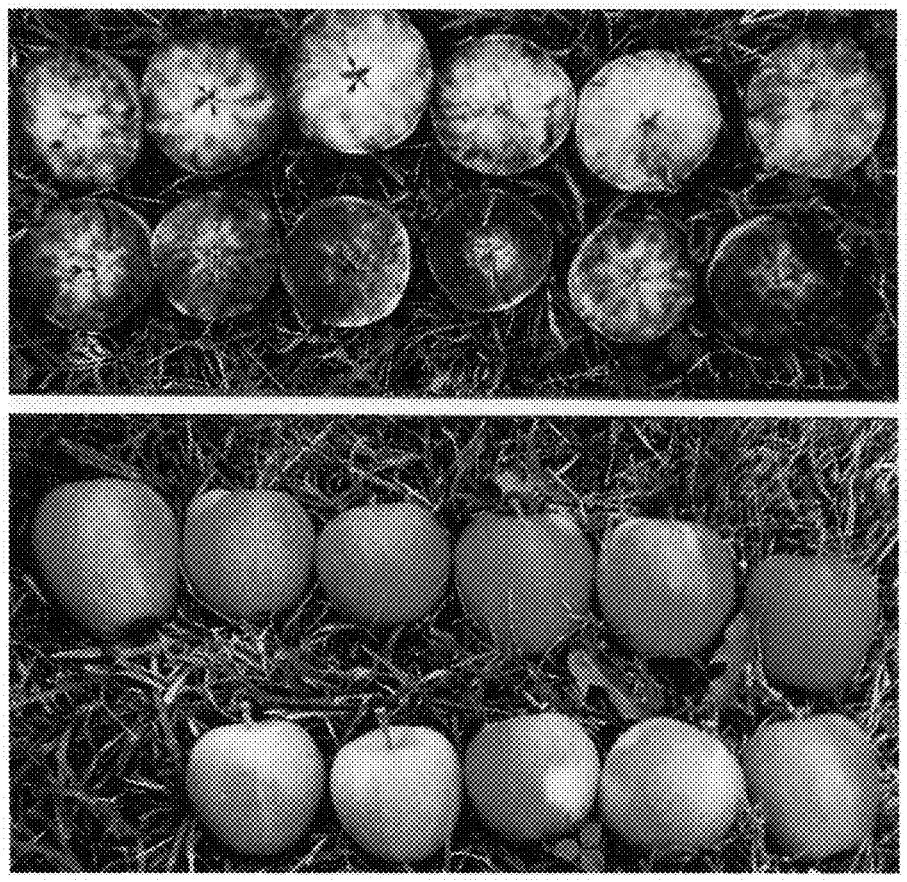
FIG. 3 shows the difference in maturity between 'Jugala' (top) and 'Mitchgla' (bottom), as evidenced by starch testing and skin color comparisons.
Figure 4:
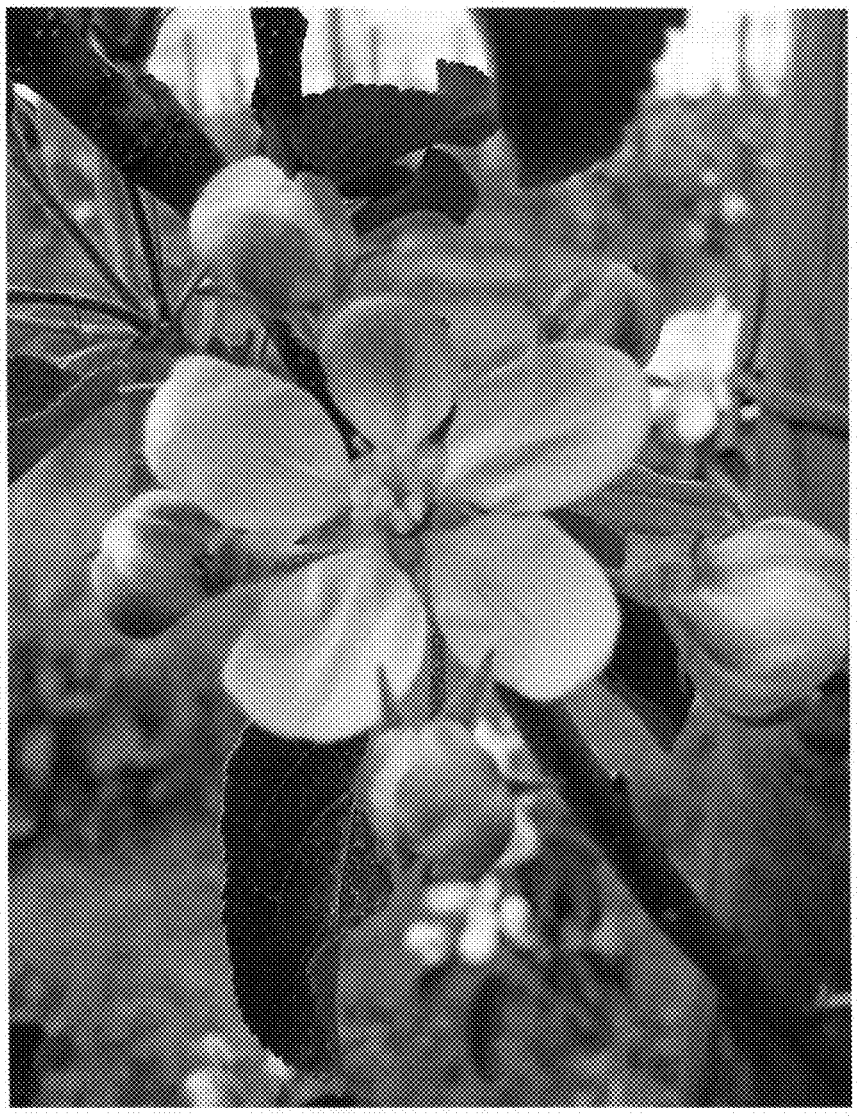
FIG. 4 shows the flowers of 'Jugala'.
Figure 5:
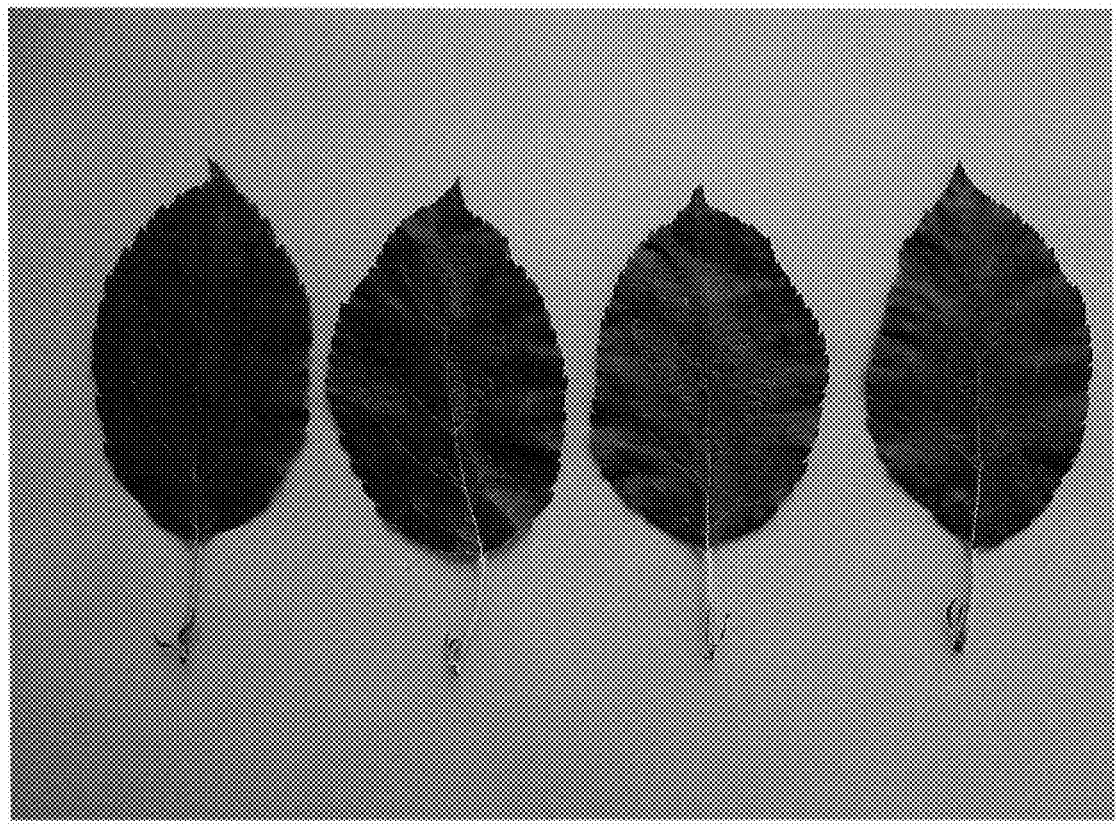
FIG. 5 shows the leaves of 'Jugala'.

The following detailed botanical description is based on observations made during the 2007 growing season at Seiches sur le Loir, France of three year old trees grown on M9 rootstock in high density plantings. All colors are described according to The Royal Horticultural Society Colour Chart. It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

Tree:
*Vigor.*—Medium (similar to Gala strains).
*Type.*—Ramified.
*Habit.*—Spreading.
*Height.*—2.20 m.
*Trunk diameter* (*at* 30 *cm above the graft*).—Medium (avg. 43 mm).
*Bark texture.*—Smooth.
*Bark coloration.*—Grey 202C.

Branch(fruiting branches located at around 1 m above the graft union).
*Length.*—Long (avg. 1.23 m).
*Diameter.*—Large (avg.18 mm).
*Crotch angle* 70° to 90° from vertical.
*Bark color.*—Grey 202C.

One year old shoot:
*Length.*—Long (avg. 45 cm).
*Color.*—Dark brown 200C.
*Pubescence* (*on upper half of the shoot*).—Medium.
*Thickness.*—Medium to large (avg. 5 mm).
*Internode length.*—Medium (avg. 30 mm).
*Pubescence.*—Medium.
*Number of lenticels.*—Medium (11 lenticels per $cm^2$).

Flower buds:
*Quantity per spur.*—3 to 6.
*Shape.*—Round to conical.
*Length.*—Small to medium (avg. 12 mm).
*Diameter.*—Small to medium (avg. 10 mm).
*Color.*—Red purple N57A.

Flowers:
*Color* (*flower buds*).—Red purple N57A.
*Diameter of fully open flower.*—Small to medium.
*Flower depth.*—15 mm.
*Relative position of petal margin.*—Overlapping.
*Number per cluster.*—5 to 6.
*Date of first bloom.*—April 17 in Loire Valley, France.
*Date of full bloom.*—April 18 in Loire Valley, France.

Petals:
*Number per flower.*—5.
*Shape.*—Ovoid.
*Length.*—Medium (avg. 16 mm).
*Width.*—Medium (avg. 12 mm).
*Apex.*—Round.
*Base.*—Conical-pointed.
*Margin*—Smooth.
*Coloration of upper surface.*—White N155C.
*Coloration of lower surface.*—White N155B.

Pistils:
*Size.*—Medium (avg. 14 cm long).
*Color.*—Yellow green N144C.

Anthers:
*Quantity.*—Numerous (avg. 14 per flower).
*Size.*—Medium (avg. 2.1 mm long).
*Presence of pollen.*—Present.
*Color of pollen.*—Yellow 3C.

Stigma:
*Size.*—Small to medium (avg. 0.5 mm diameter).
*Color.*—Yellow green 150B.

Style:
*Size.*—Long (avg. 9 mm).
*Color.*—Yellow green 145A.

Ovary:
*Size.*—Medium (avg. 2 mm diameter).
*Color.*—Green 140A.

Pedicel:
*Length.*—Medium to long (avg. 22 mm).
*Diameter.*—Quite thin (avg. 1.4 mm).
*Color.*—Green 143B.

Sepals:
*Quantity.*—5.
*Coloration* (*upper and lower surfaces*).—Green 143C.
*Shape.*—Conical pointed.
*Length.*—8 mm.
*Width.*—3 mm.
*Margin.*—Smooth.
*Apex.*—Pointed.

Leaves:
*Shape.*—Elliptic.
*Length* (*petiole not included*).—Medium to long (avg. 98 mm).
*Width.*—Medium (avg. 55 mm).
*Length/width ratio.*—Medium (1.78).
*Blade margin.*—Biserrate.
*Apex.*—Acuminate.
*Base shape.*—Oblique.
*Color of upper surface.*—Dark green 136A.
*Color of lower surface.*—Light green 137C.
*Attitude in relation to shoot.*—Outward to downward.

Petiole:
*Length.*—Medium (avg. 27 mm).
*Diameter.*—Medium (avg. 1.7 mm).
*Coloration.*—Light green 141D.

Fruit:
*Quantity per cluster.*—1 to 3.
*Size.*—Small to medium (avg. 72 mm diameter).
*Weight.*—Medium (avg. 190 g).
*Ratio of height to width.*—Medium (1.02).
*General shape in profile.*—Conic.
*Position of maximum diameter.*—In middle.
*Ribbing.*—Moderate.
*Crowning at calyx end.*—Moderate.
*Size of eye.*—Medium (avg. 13 mm diameter).
*Aperture of eye.*—Partially open.
*Length of sepal.*—Medium to long (avg. 4 mm).
*Bloom of skin.*—Weak.
*Greasiness of skin.*—Weak.
*Skin thickness.*—Similar to 'Gala'.
*Locules.*—Similar to 'Gala'.
*Background color of skin.*—Light yellow 8C
*Amount of over color.*—Medium.
*Over color of skin.*—Red 41A.
*Intensity of over color.*—Medium.
*Pattern of over color.*—Solid flush with stripes.
*Amount of russet around stalk cavity.*—Weak.
*Amount of russet on cheeks.*—Absent.
*Area of russet around eye basin.*—Absent or very weak.
*Length of stalk.*—Long (avg. 29 mm).
*Thickness of stalk.*—Medium (avg. 2.2 mm).
*Depth of stalk cavity.*—Medium (avg. 16 mm).
*Width of stalk cavity.*—Narrow (avg. 12 mm).
*Depth of eye basin.*—Medium (avg. 9 mm).
*Width of eye basin.*—Narrow (avg. 18 mm).
*Firmness of flesh.*—Medium to firm.
*Flesh texture.*—Medium to fine.

*Aroma.*—Moderately aromatic and slightly sweet.
*Juiciness.*—Medium to high.
*Brix.*—11° brix minimum at harvest time.
*Flesh coloration.*—Light yellow 4D.
*Stem coloration.*—Red 53A.

Seeds:
*Quantity per fruit.*—5 on average.
*Shape.*—Truncate ovoid.
*Coloration.*—Dark brown 165A.

Disease/pest resistance/susceptibility: None noted.

Harvest:
*Time for harvest.*—Early (mid-August).
*Number of picks.*—One to two picks.

Chilling requirements: Similar to 'Gala'.

Fruit keeping quality: Similar to 'Gala'.

I claim:

1. A new and distinct apple tree substantially as described and illustrated herein.

* * * * *